United States Patent [19]

Tamagawa

[11] 4,436,827
[45] Mar. 13, 1984

[54] DETECTING PARTICLE AGGLUTINATION WITH VESSEL HAVING INCLINED, STEPPED BOTTOM SURFACE

[75] Inventor: Akira Tamagawa, Hino, Japan

[73] Assignee: Olympus Optical Co. Ltd., Japan

[21] Appl. No.: 401,565

[22] Filed: Jul. 26, 1982

[30] Foreign Application Priority Data

Jul. 30, 1981 [JP] Japan ................. 56-118504

[51] Int. Cl.³ ............ G01N 33/54; G01N 33/80; G01N 21/05; G01N 31/02
[52] U.S. Cl. .................... 436/534; 73/64.1; 356/246; 356/440; 422/73; 422/102; 424/11; 436/63; 436/164; 436/533; 436/805; 436/807
[58] Field of Search ............... 422/73; 424/11; 436/533, 534, 805, 807, 63, 164; 356/246, 440; 73/64.1

[56] References Cited

U.S. PATENT DOCUMENTS 3,334,018  8/1967  Smythe ..................... 424/11
4,303,616 12/1981  Kano ..................... 422/73 X
4,373,931  2/1983  Takekawa ............... 422/73 X Primary Examiner—Sidney Marantz
Attorney, Agent, or Firm—Parkhurst & Oliff

[57] ABSTRACT

A particle agglutination reaction is detected with the aid of a reaction vessel of flow cell type having an inlet, an outlet and an inclined passage communicating the inlet and outlet to each other. A test liquid containing particles is supplied into the passage via the inlet and is retained stationary therein for a given time period. Particles descending upon an inclined bottom surface of the passage form at first a stable base layer due to regular steps formed in the bottom surface. When a particle agglutination reaction has occurred, a uniformly deposited particle pattern is formed on the inclined bottom surface, while in case of non-agglutination reaction, the particles descending upon the inclined bottom surface roll down along the base layer and are collected at the lowermost portion of the passage. By detecting the particle pattern formed on the inclined bottom surface, it is possible to detect the agglutination reaction accurately.

12 Claims, 6 Drawing Figures

DETECTING PARTICLE AGGLUTINATION WITH VESSEL HAVING INCLINED, STEPPED BOTTOM SURFACE

BACKGROUND OF THE INVENTION

This invention relates to a method for detecting a particle agglutination reaction with the aid of a flow cell type reaction vessel.

Various methods have been proposed for detecting a particle agglutination reaction in order to identify various kinds of blood types and the existence or non-existence of various kinds of antigens and antibodies.

In one known method, winecup-shaped reaction vessels are used and in another known method a plate having a number of reaction vessels with conical bottoms is used. These known methods may be classified as a batch system in which successive samples and a reagent are delivered into respective reaction vessels to form test liquids therein. There has been also developed an agglutination reaction detecting method of a flow cell type in which successive test liquids are supplied to a flow cell. One of the known examples of such an agglutination reaction detecting apparatus will be further explained in detail with reference to FIG. 1.

In FIG. 1, the apparatus comprises a coiled tube 1, a tube assembly 2 including branch tubes 2a, 2b, 2c and 2d, a light source 3 and a light receiving element 4 arranged on both sides of the branch tube 2d. It should be noted that at least the branch tube 2d is made of transparent material. Successive test liquids $T_1$, $T_2$ ... containing particles such as blood cells are supplied into the coiled tube 1 with air bubbles $A_1$, $A_2$ ... interposed between successive test liquids. In this manner, the test liquids can be supplied to the tube assembly 2 without causing contamination between successive test liquids. While the test liquid is passed through the coiled tube 1, the agglutination reaction proceeds. If the agglutination reaction occurs, the particles are agglutinated and the thus agglutinated particles descend quickly into the branch tubes 2a and 2b. Therefore, the test liquid fed into the branch tube 2d which serves as a measuring chamber contains a smaller amount of particles. Contrary to this, when there is no agglutination reaction, the test liquid supplied into the branch tube 2d contains a greater amount of particles, because the amount of particles which descend into the branch tubes 2a and 2b is smaller. Therefore, by measuring the transmittivity or absorbance of the test liquid in the branch tube 2d by means of the light source 3 and light receiving element 4, it is possible to detect whether the agglutination reaction has occurred or not. That is to say, when the agglutination reaction occurs, the transmittivity becomes larger, whilst in case of non-agglutination reaction, in transmittivity becomes smaller.

However, in the known apparatus shown in FIG. 1, the detection of the agglutination reaction could not be effected in the coiled tube 1 serving as a reaction chamber and it is necessary to provide the measuring tube assembly 2 separately from the reaction vessel 1. Therefore, the construction becomes complicated and very large. Further, if the agglutination reaction is weak, large masses of particles are not formed and thus, the descending speed is slow, so that the amount of the particles descending into the branch tubes 2a and 2b is small. Therefore, it is difficult to differentiate the weak agglutination reaction from non-agglutination reaction. Moreover, the measured results might be subjected to variation or fluctuation in the density of particles in the test liquids, i.e. errors in amounts of delivered samples and reagents. Due to the above problems, it is difficult to detect precisely the agglutination reaction by means of the known apparatus. It should be further noted that since the known apparatus does not directly detect the agglutinated particles per se, its detection accuracy is inherently low.

SUMMARY OF THE INVENTION

The present invention has for its object to provide a novel and useful method for detecting an agglutination reaction in an accurate and reliable manner, in which agglutinated particles descending on bottom surface of a reaction vessel serving as a flow cell can be directly detected.

According to the invention, a method for detecting a particle agglutination reaction with the aid of a flow cell type reaction vessel comprises:

a step of supplying a test liquid containing particles into a reaction vessel having a bottom surface, a part of which is inclined and has formed therein steps for forming a stable base layer of particles descending thereupon;

a step of retaining the test liquid stationary in the reaction vessel for a predetermined time; and a step of detecting photoelectrically a particle agglutination pattern formed by agglutinated particles settled on said bottom surface.

The present invention also relates to a reaction vessel of the flow cell type which is used in the method for detecting a particle agglutination reaction.

According to the invention, a reaction vessel of flow cell type for use in a particle agglutination detecting method comprises:

a tubular main body made of transparent material;

an inlet formed at one end of the tubular main body, a test liquid containing particles being supplied into the reaction vessel through said inlet;

an outlet formed at the other end of the tubular main body, the test liquid being discharged from the reaction vessel through said outlet;

a passage communicating said inlet to said outlet and including an inclined section in whose bottom surface are formed a number of steps in such a manner that a stable base layer of particles descending upon the bottom surface is formed.

DESCRIPTION OF THE PREFERRED EMBODIMENTS

Figure 2A:
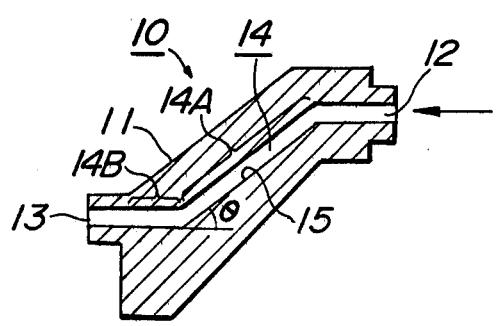
FIGS. 2A and 2B are cross section and front views illustrating one embodiment of the reaction vessel of flow cell type according to the invention.
Figure 2B:
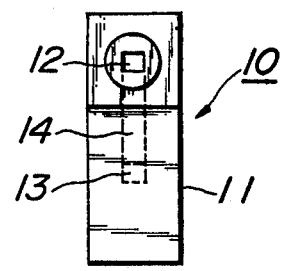
Figure 3:
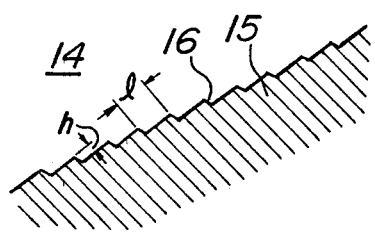
FIG. 3 is an enlarged cross section depicting the construction of the inclined bottom surface of the reaction vessel.

FIGS. 2A and 2B show an embodiment of the reaction vessel of flow cell type according to the invention. The reaction vessel 10 comprises a tubular main body 11 made of a transparent material, such as glass or plastics. At opposite ends of the tubular body 11 there are formed inlet 12 and outlet 13. The inlet and outlet are communicated to each other by means of a passage 14 formed in the tubular body 11. As shown in FIG. 2A, a middle section 14A of the passage 14 is inclined by a suitable angle $\theta$ with respect to horizontal and a number of regular steps are formed in the bottom wall 15 of the inclined section of the passage 14. As illustrated in FIG. 3 on an enlarged scale, the steps 16 formed in the inclined bottom surface 15 have the shape of a triangle. The inlet 12, the outlet 13 and the passage 14 communicated thereto have a rectangular cross section as shown in FIG. 2B. Therefore, the bottom surface 15 of the passage 14 is also flat, provided the very small steps 16 formed therein are neglected. In one example of the reaction vessel 10 for use in detection of agglutination reaction of human blood cells, the inclination angle $\theta$ may be set to about 27°, length l and height h of a step 16 may be set to 5-200 μm and 2-50 μm, respectively.

Now the method for detecting the particle agglutination reaction with the aid of the above explained reaction vessel of flow cell type will be explained. It is assumed that a blood type such as the A, B, O system is to be detected. A whole blood sample is taken out of a patient and blood cells contained therein are extracted by centrifuge, for example. Then the extracted blood cells are mixed with a reagent containing predetermined anti-bodies such as anti-A or anti-B serum to form a test liquid. Then the test liquid thus formed is introduced into the reaction vessel 10 via the inlet 12 and is kept stationary therein for a given time of several minutes to several tens of minutes. During this time period, at first blood cells descending upon the bottom surface 15 of the passage 14 are retained thereon due to the steps 16 to form a stable base layer. When the agglutination reaction occurs, agglutinated particles descending on the bottom surface are retained on the base layer and a uniformly deposited particle pattern is clearly formed on the bottom surface. Contrary to this, when no agglutination reaction occurs, non-agglutinated particles descending on the bottom surface 15 roll down along the base layer and are collected at the lowest section 14B of the passage 14. In this manner, the deposited particle patterns formed on the inclined bottom surface in case of the agglutination and non-agglutination differ from each other remarkably and thus, by detecting the particle patterns on the inclined bottom surface it is possible to detect the agglutination reaction in an accurate manner. The detection can be effected with the naked eye or by a photoelectric device.

Figure 1:
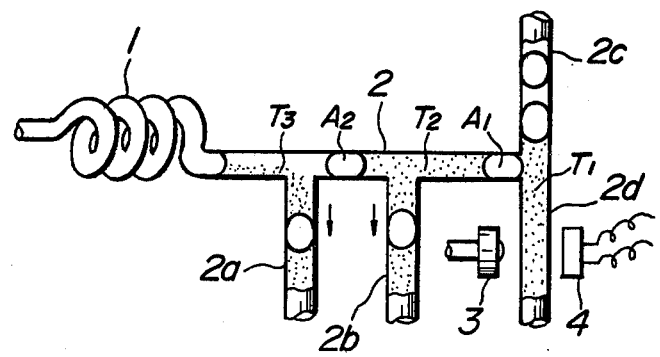
FIG. 1 is a schematic view showing a known apparatus for detecting a particle agglutination reaction with the aid of a flow cell.

According to the reaction vessel of the present invention, since the reaction and detection are carried out in the same passage 14, it is not necessary to provide the reaction chamber and the detection chamber separately as in the case of the known apparatus shown in FIG. 1 and therefore, the whole construction can be made simple and small. Further, since the test liquid is contained in the inclined passage 14, the particles can descend on the bottom wall 15 after traveling very short distances, the particle pattern can be formed on the bottom surface within a very short time and the necessary time for effecting the analysis can be materially shortened.

Figure 4:
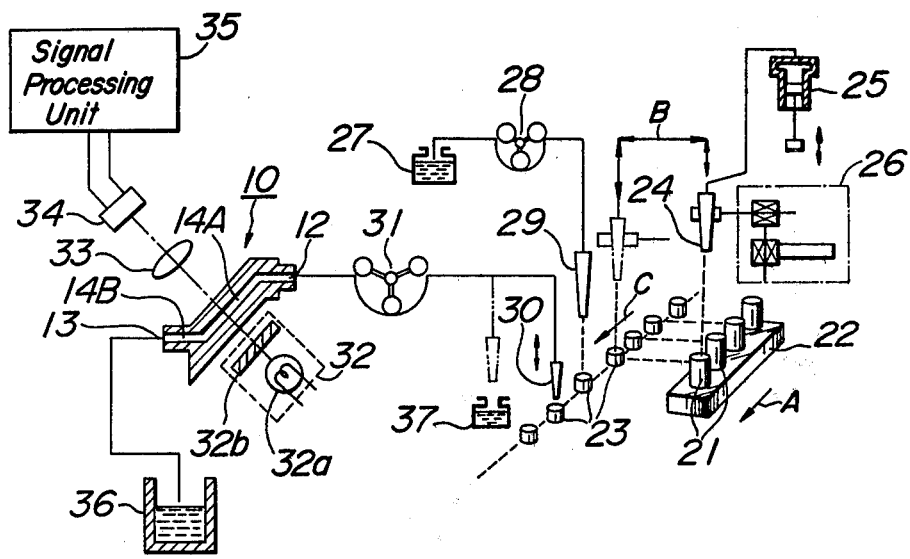
FIG. 4 is a schematic view showing an embodiment of the apparatus for carrying out the detection method according to the invention.

FIG. 4 illustrates an apparatus for detecting the particle agglutination reaction according to the invention. The apparatus comprises the reaction vessel 10 of the flow cell type shown in FIGS. 2A and 2B. Samples are contained in test tubes 21 which are set in a rack 22 which is moved in a stepwise manner in a direction shown by arrow A. A given amount of a sample in a test tube 21 is delivered into a cup 23 by means of a nozzle 24 and a syringe pump 25 connected thereto. The nozzle 24 is moved by means of a driving mechanism 26 up and down as well as right and left as illustrated by arrows B. The cups 23 are moved in a stepwise manner in a direction shown by an arrow C in synchronization with the rack 22.

Next, a given amount of a reagent contained in a bottle 27 is delivered by means of a rotary pump 28 and a nozzle 29 into the cup 23 to form a test liquid. Then the test liquid in the cup 23 is supplied by means of a nozzle 30 and a rotary pump 31 into the reaction veessel 10 through the inlet 12 and is retained therein for a predetermined time. During this stand-still time, the particle pattern is formed on the inclined bottom surface of the passage 14. The particle pattern is photoelectrically detected by means of a light source 32 including a lamp 32a and a filter 32b, a lens 33 and a light detector 34. The filter 32b has such a spectrum property that it selectively transmits a light flux which is predominantly absorbed by the particles. A photoelectric signal produced by the light detector 34 is supplied to a signal processing unit 35 and an analytical result is printed out or displayed.

After the photoelectric detection, the test liquid in the reaction vessel 10 is discharged into a waste bottle 36 by driving the rotary pump 31. Then, a wash liquid in a bottle 37 is flowed through the reaction vessel 10 to wash the reaction vessel. In this manner, the successive test liquids formed in the successive cups 23 can be delivered into the reaction vessel 10 and the agglutination reaction can be detected for successive test liquids without contamination.

Figure 5:
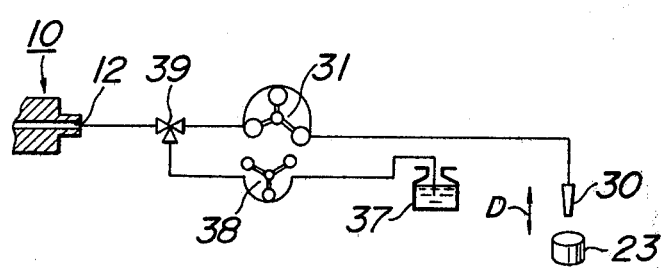
FIG. 5 is a schematic view illustrating an embodiment of a device for washing the reaction vessel.

The present invention is not limited to the embodiment explained above, but many modifications and alternations may be conceived by those skilled in the art within the scope of the invention. For instance, the reaction vessel 10 may be washed in a manner illustrated in FIG. 5. In FIG. 5, the wash liquid contained in the bottle 37 is supplied to the reaction vessel 10 by means of a rotary pump 38 and a three-way valve 39. By means of such a construction, the nozzle 30 for sucking the test liquid in the cup 23 is sufficient to move up and down as shown by an arrow D.

In the embodiment illustrated in FIG. 4, the particle pattern is detected by measuring a transmittivity of the inclined section 14A of the passage 14. It is also possible to detect the particle pattern by measuring transmittivities at the inclined section 14A and the lowermost section 14B of the passage 14 and by deriving a difference therebetween. In case of the agglutination reaction, the difference is very small, while the difference becomes extremely large in the case of non-agglutination reaction. Therefore, it is possible to effect the detection precisely, even if the agglutination reaction is weak.

Further, it should be noted that the steps formed in the inclined bottom surface may have any desired shape.

The advantages attained by the present invention can be summarized as follows.

(1) Since the reaction vessel serves both as the reaction chamber and the detection chamber, the reaction vessel can be constructed in a simple and compact manner.

(2) Since the reaction vessel also serves as the flow cell, the test liquids can be processed easily and the whole construction of the detection apparatus can be made simple.

(3) Since the stable base layer of particles can be formed on the inclined bottom surface due to the steps formed therein, the particle agglutination patterns can be formed clearly and thus, the detection accuracy can be increased.

(4) The passage in which the test liquid is retained for a given time has a small depth, the particles can soon descend on the bottom surface and therefore, the given stand-still time can be shortened.

What is claimed is:

1. A method for detecting a particle agglutination reaction with the aid of a flow cell type reaction vessel comprising:
    supplying a test liquid containing particles into a reaction vessel which comprises a tubular body having an inlet, an outlet arranged below said inlet and a passage communicating between said inlet and said outlet, said tubular body being inclined to define an inclined bottom surface by an inner wall of said passage, said bottom surface having a plurality of steps formed therein for forming a stable base layer of particles descending thereon;
    keeping the test liquid stationary in the reaction vessel for a predetermined time; and
    detecting a particle agglutination pattern formed by agglutinated particles settled on the inclined bottom surface.

2. A method according to claim 1, wherein said detecting step is carried out by photoelectrically detecting the particle agglutination pattern formed on the inclined bottom surface with the aid of a light source and a light detector.

3. A method according to claim 2, wherein the photoelectrically detecting step is effected by means of a light flux which is selectively absorbed by the particles.

4. A method according to claim 2, wherein said reaction vessel has a lowermost bottom section at the lower end of said inclined bottom surface and the particle agglutination pattern is detected by measuring transmittivities at the inclined bottom surface and at the lowermost bottom section into which non-agglutinated particles are collected, and by deriving a difference between the measured transmittivities.

5. A method according to claim 1, wherein successive test liquids are supplied into the reaction vessel, and the reaction vessel is washed by passing a wash liquid therethrough each time after the test liquid is discharged from the reaction vessel.

6. A flow cell type reaction vessel for use in a method for detecting a particle agglutination reaction, comprising:
    a tubular main body made of transparent material, said tubular body being inclined by a predetermined angle;
    an inlet formed at an upper end of the tubular main body, supplying a test liquid containing particles into the reaction vessel;
    an outlet formed at a lower end of the tubular main body for discharging the test liquid from the reaction vessel; and
    a passage communicating said inlet to said outlet, comprising an inclined section with a bottom surface in which a number of steps are formed in such a manner that particles decending upon the inclined bottom surface form a stable base layer thereon.

7. A reaction vessel according to claim 6, wherein said steps are formed regularly in the inclined bottom surface.

8. A reaction vessel according to claim 6, wherein said inclined bottom surface makes an angle of about 20° to 40° with respect to the horizontal plane.

9. A reaction vessel according to claim 7, wherein said step has a length of 5 to 200 $\mu$m and a height of 2 to 50 $\mu$m.

10. A reaction vessel according to claim 6, wherein said passage has a rectangular cross section.

11. A reaction vessel according to claim 6, wherein said passage has a horizontal section at a portion communicated with the outlet.

12. A reaction vessel according to claim 8, wherein said angle is 27°.

* * * * *